(12) United States Patent
Ganyi

(10) Patent No.: US 9,427,177 B2
(45) Date of Patent: Aug. 30, 2016

(54) FALL DETECTION METHODS AND DEVICES

(75) Inventor: Tibor Ganyi, Hellbuehl (CH)

(73) Assignee: Fidelity Investment Corporation, Reading, PA (US)

( * ) Notice: Subject to any disclaimer, the term of this patent is extended or adjusted under 35 U.S.C. 154(b) by 480 days.

(21) Appl. No.: 13/248,698

(22) Filed: Sep. 29, 2011

(65) Prior Publication Data

US 2012/0259577 A1    Oct. 11, 2012

Related U.S. Application Data

(60) Provisional application No. 61/473,936, filed on Apr. 11, 2011.

(51) Int. Cl.
| | |
|---|---|
| *G01C 9/00* | (2006.01) |
| *G01C 19/00* | (2013.01) |
| *A61B 5/11* | (2006.01) |
| *G08B 21/04* | (2006.01) |
| *A61B 5/00* | (2006.01) |

(52) U.S. Cl.
CPC ............ *A61B 5/1117* (2013.01); *A61B 5/1122* (2013.01); *G08B 21/043* (2013.01); *G08B 21/0446* (2013.01); *A61B 5/6822* (2013.01); *A61B 5/6831* (2013.01); *A61B 2560/0257* (2013.01); *A61B 2562/0219* (2013.01)

(58) Field of Classification Search
CPC ............ G01C 9/06; G01C 9/00; G01C 9/12; G01C 9/20
USPC ........................................................ 702/154
See application file for complete search history.

(56) References Cited

U.S. PATENT DOCUMENTS

| | | | |
|---|---|---|---|
| 3,667,293 A | | 6/1972 | Moore |
| 4,858,622 A | | 8/1989 | Osterweil |
| 5,777,899 A | * | 7/1998 | Kumagai ........................ 702/94 |
| 6,433,690 B2 | | 8/2002 | Petelenz et al. |
| 7,095,331 B2 | | 8/2006 | Lehrman et al. |
| 7,421,369 B2 | * | 9/2008 | Clarkson ....................... 702/150 |
| 7,423,537 B2 | | 9/2008 | Bonnet et al. |
| 7,509,220 B2 | * | 3/2009 | Hedtke ........................ 702/104 |

(Continued)

FOREIGN PATENT DOCUMENTS

| | | |
|---|---|---|
| DE | 102009019767 A1 | 11/2010 |
| EP | 1632920 A1 | 3/2006 |

(Continued)

OTHER PUBLICATIONS

Data sheet, KXTF9-1026 +/− 2g Tri-axis Digital Accelerometer. 41 pages. Kionix, Inc., Ithaca, NY, Jul. 2010.

(Continued)

*Primary Examiner* — Michael Nghiem
(74) *Attorney, Agent, or Firm* — Coats & Bennett, P.L.L.C.

(57) ABSTRACT

A fall detection device includes a fall detection circuit to detect a fall by a user and a verification circuit to verify the initial indication of a fall from the fall detection circuit. The device is sized to be worn by the user and includes an orientation sensor to track the orientation of the device relative to one or more axes. The device averages the average inclination values for one or more axes for time periods before, during, and after the fall. A fall is determined to have occurred when differences in the average values of the inclination values exceed threshold values.

19 Claims, 5 Drawing Sheets

(56) References Cited

U.S. PATENT DOCUMENTS

| | | |
|---|---|---|
| 7,612,681 B2 | 11/2009 | Azzaro et al. |
| 7,712,365 B1 | 5/2010 | James |
| 7,714,728 B2 | 5/2010 | Koblasz |
| 7,857,771 B2 | 12/2010 | Alwan et al. |
| 7,893,844 B2 | 2/2011 | Gottlieb |
| 7,916,066 B1 | 3/2011 | Osterweil |
| 2001/0004234 A1* | 6/2001 | Petelenz et al. ............ 340/539 |
| 2006/0049950 A1 | 3/2006 | Lockhart |
| 2006/0139166 A1 | 6/2006 | Choutier et al. |
| 2006/0260397 A1* | 11/2006 | Kim et al. .................... 73/488 |
| 2006/0279426 A1 | 12/2006 | Bonnet et al. |
| 2007/0229286 A1 | 10/2007 | Huang |
| 2008/0129518 A1 | 6/2008 | Carlton-Foss |
| 2008/0272918 A1 | 11/2008 | Ingersoll |
| 2009/0224925 A1 | 9/2009 | Gannot et al. |
| 2009/0292227 A1* | 11/2009 | Scholten et al. ............ 600/595 |
| 2010/0121226 A1 | 5/2010 | Ten Kate et al. |
| 2010/0191408 A1* | 7/2010 | Boylston ................ G01C 9/00  701/31.4 |
| 2011/0077865 A1* | 3/2011 | Chen .................... A61B 5/1117  702/3 |

FOREIGN PATENT DOCUMENTS

| | | |
|---|---|---|
| EP | 1731098 A1 | 12/2006 |
| EP | 1870037 A1 | 12/2007 |
| WO | 2004100092 A2 | 11/2004 |
| WO | 2009142975 A1 | 11/2009 |
| WO | 2010105379 A1 | 9/2010 |
| WO | 2010125096 * | 11/2010 |

OTHER PUBLICATIONS

Tuck, K. "Tilt Sensing Using Linear Accelerometers." Application Note. Freescale Semiconductor, Inc. Tempe, AZ, Jun. 2007.

"Tilt Sensing with Kionix MEMS Accelerometers." Application Note. Kionix, Inc., Ithaca, NY, 2005.

International Search Report mailed Jul. 31, 2012 in re PCT Application No. PCT/IB2012/051751.

* cited by examiner

FALL DETECTION METHODS AND DEVICES

RELATED APPLICATION

The present application claims priority to previously-filed U.S. provisional application No. 61/473,936 filed on Apr. 11, 2011 and herein incorporated by reference in its entirety.

BACKGROUND

The present invention relates generally to fall detection devices and, more particularly, to techniques for avoiding false positive alarms in fall detection devices.

There are many applications today for fall detection devices that determine when a user has fallen. Examples include but are not limited to use by a senior living alone, and a work place environment with potentially dangerous conditions.

Many devices are currently on the market for determining fall detection. However, these devices have a high rate of error in which a fall is determined even when the user has not actually fallen. These false positive errors may occur when a user walks down steps, rides in an elevator, runs, or jumps. These false positive errors result in an alarm being sent to a third party, and may cause emergency personnel to arrive with the expectation of finding an injured person.

These false positive errors often make persons reluctant to wear the devices. Persons do not want the hassle of constantly remembering to limit physical activity in a particular manner to prevent the occurrence of false positive errors. Persons may also not want the embarrassment of emergency personnel responding to their location when there is no fall occurrence.

Persons may also be reluctant to wear the devices because of their size. Many of the devices are large and cumbersome to wear for the user. The size may cause the devices to be uncomfortable, or to interfere with the user's normal routine. Further, the devices may be conspicuous and draw attention to the fact that the user is wearing a fall detection device. Unwanted attention may be particularly frustrating for senior users who want to maintain their independence.

Current devices may also not be able to detect slow falls by the user. Slow falls may occur when the user partially holds himself up during a fall resulting in an extended time period from the start of the fall until the fall ends.

SUMMARY

The present application is directed to methods and apparatus to avoid false positive alarms in a fall detection device. The fall detection device according to one embodiment includes a conventional fall detection sensor to provide an initial indication of a fall. The fall detection sensor may comprise a speed sensor, pressure sensor, accelerometer, gyroscope, or a combination thereof. A low-G accelerometer is configured as an inclinometer to measure the inclination of the device in one or more axes relative to the earth's gravity before, during, and after the fall. When an initial indication of a fall is given, the measurements for all three axes are compared to confirm that a fall has occurred. More particularly, the device averages the measurements for all three axes before the fall, during the fall, and after the fall, and compares the averages before the fall to the averages during and/or after the fall. The averages before the fall provide the baseline for comparison. The fall is confirmed and an alarm is generated if the difference in the averages for at least one axis exceeds a predetermined threshold. If the averages during and after the fall remain within predetermined limits of the average before the fall, the initial fall indication is canceled and no alarm is generated.

The averaging of the measurements performs a form of filtering to filter out the dynamic component of the inclination measurements and obtain the static component of the user's orientation despite movements of the user. Thus, the device can provide accurate results while being worn on a user's extremity, such as the user's arm or leg, that normally experiences large movements and large changes in orientation. This feature enables the concealment of the fall detection device in a wristwatch or wristband to counter the fact that fall detection devices are often not worn because they are indiscreet.

One embodiment is directed to a method of detecting a fall by a user that includes receiving an initial indication of a fall, measuring an inclination of a device worn by the user relative to one or more different axes at a first plurality of time instants before the fall and for a second plurality of time instants during the fall. The method includes responsive to the initial indication, comparing the inclination of the device during the fall to the inclination of the device before the fall, and verifying that a fall occurred based on the comparison.

Another embodiment is directed to a method of detecting a fall by a user that includes receiving an initial indication of a fall, measuring an inclination of a device worn by the user relative to one or more different axes at a first plurality of time instants in a first time period before the initial indication, a second plurality of time instants in a second time period including the initial indication, and a third plurality of time instants in a third time period after the initial indication. The method includes calculating, from the measurements, an average inclination for the one or more axes for the first time period, the second time period, and the third time period. The method includes calculating a first difference between the average inclination for the second time period and the average inclination for the first time period for at least one of the axes. The method includes calculating a second difference between the average inclination for the third time period and the average inclination for the first time period for at least one of the axes. The method includes verifying that a fall has occurred if the first or second difference exceeds a threshold.

One embodiment includes a fall detection device that is worn by a user. The device includes a fall detection circuit to provide an initial indication of a fall, and an orientation sensor to measure an inclination of the user. The device includes a verification circuit for verifying that a fall has occurred with the verification circuit configured to receive an initial indication of a fall from the fall detection circuit, determine an inclination of the device relative to one or more different axes for a first plurality of time instants before the fall and for a second plurality of time instants during the fall, compare, responsive to the initial indication, the inclination of the device during the fall to the inclination of the device before the fall, and to verify that a fall occurred based on the comparison.

The various aspects of the various embodiments may be used alone or in any combination, as is desired.

DETAILED DESCRIPTION

The present application is directed to methods and devices for detecting a fall by a user. The system includes a fall detection device worn by the user that includes a fall detection sensor, such as a pressure sensor, and an accelerometer configured as an inclinometer to detect the orientation of the device in one or more axes. The accelerometer is used to detect false positive indications generated by the fall detection sensor. When a fall is initially detected, the device uses the orientation data collected before, during, and after the fall to confirm that a fall has occurred. In one embodiment, the device compares the average orientation of the device during the fall to the average orientation before the fall. In some embodiments, the device may also compare the average orientation of the device after the fall to the average orientation before the fall. Based on the comparisons, it is determined whether a fall has in fact occurred. Thus, the false positive indications by the fall detection sensor can be identified.

Figure 1:
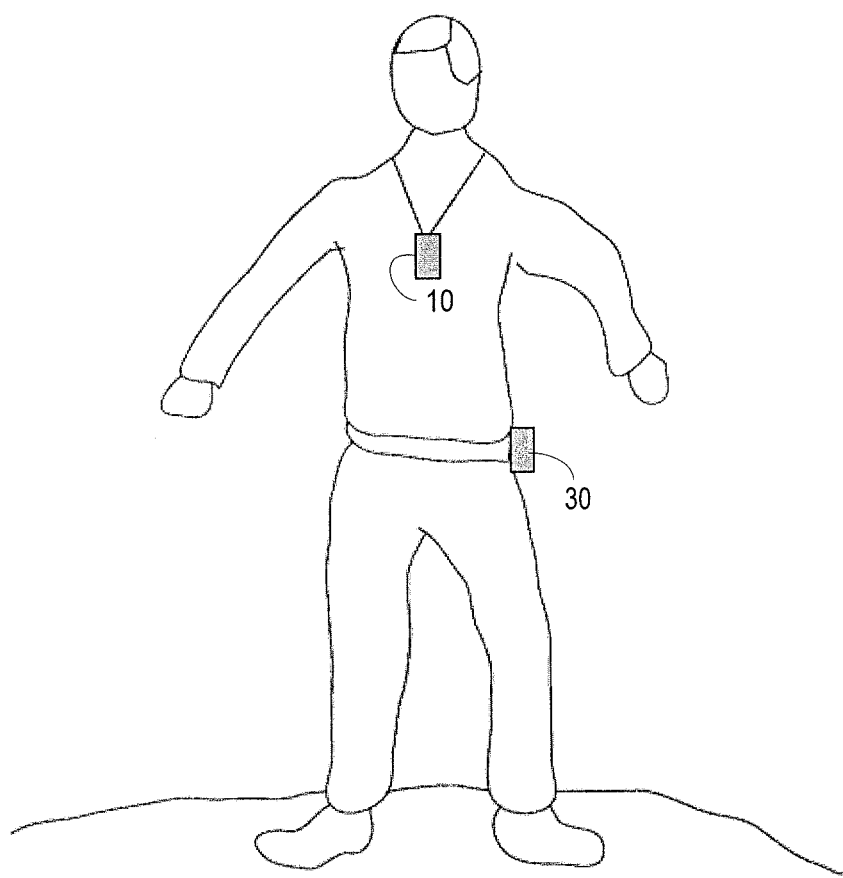
FIG. 1 is a front view of a user wearing a fall detection device.

FIG. 1 illustrates a device 10 worn by a user. The device 10 is sized to be relatively inconspicuous on the body of the user. The device 10 may be enclosed in a housing 19 (FIG. 2) that protects the device 10. The housing 19 may also include aesthetically pleasing aspects (e.g., surface designs, color) to give the appearance of jewelry, watch, or other similar features that may be normally worn by the user. The housing 19 may be configured to receive a chain to be worn as a necklace, or may include a fastener to be worn as a pin. The device 10 may also receive a band that secures the device 10 to the user's arm or leg. The device 10 can be worn on the trunk of the user, or on one of the user's extremities. The device 10 may also be incorporated into a watch or other useful and less conspicuous device to draw attention away from its main fall detection function. In some embodiments, the device 10 may include a remote unit 30 that contains some of the components as hereinafter described.

Figure 2:
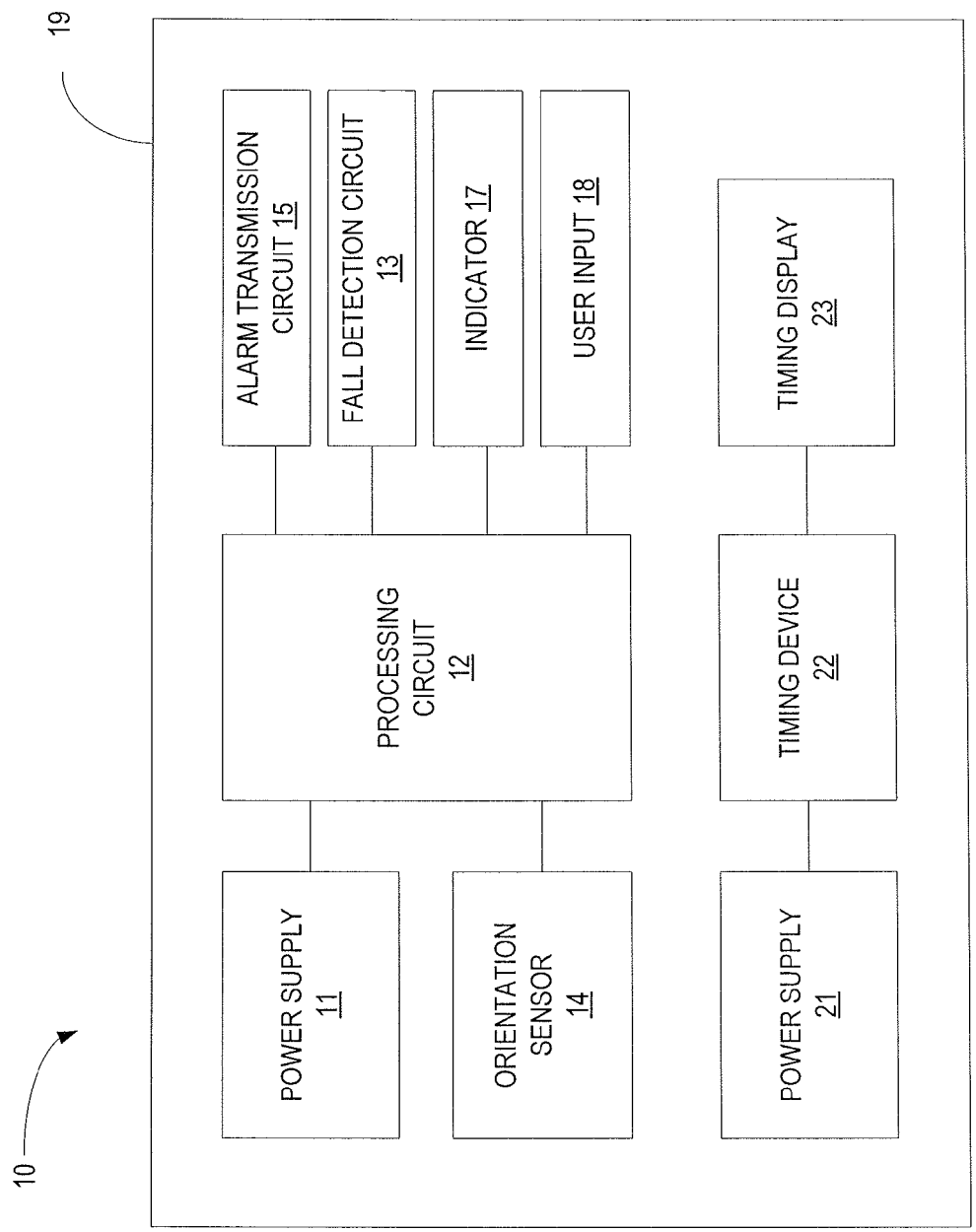
FIG. 2 is a schematic view of a fall detection device.

FIG. 2 is a schematic representation of the device 10 illustrating the main functional components. The device 10 generally includes a power supply 11, processing circuit 12, fall detection circuit 13, orientation sensor 14, and alarm transmission circuit 15, an indicator 17, and a user input device 18. In one embodiment, all of the components are contained within a single housing 19. However, some embodiments may separate components in two or more housings. For example, the fall detection circuit 13 may be contained in a remote unit 30 as shown in FIG. 1.

The processing circuit 12 provides the primary logic for detecting and confirming falls. The processing circuit 12 may comprise one or more microprocessors, hardware, firmware, or a combination thereof. The processing circuit 12 receives inputs from the fall detection circuit 13 and orientation sensor 14 and uses these inputs as hereinafter described to detect the occurrence of a fall. The processing circuit 12 outputs an alarm signal to the alarm transmission circuit 15 for transmission to a base unit (not shown) if a fall is detected. In some embodiments, the device 10 may include an indicator 17 disposed on the housing 19 to indicate to the user that an alarm signal has been sent, and a user input 18, (e.g., button) to receive a user input to cancel an alarm.

The fall detection circuit 13 comprises one or more sensors for detecting conditions indicating that a fall has occurred. In one embodiment, the fall detection circuit 13 includes one or more pressure sensors that measure atmospheric pressure. The pressure sensor(s) senses changes in the atmospheric pressure that occurs during a fall by the user. One type of fall detection circuit 13 is disclosed in WO 2010/105379. The fall detection circuit 13 may also comprise one or more motion sensors, accelerometers, and gyroscopes. The fall detection circuit 13 may include processing circuits to process the sensor outputs and provide a fall indication to the processing circuit 12. Alternatively, the fall detection circuit 13 may forward raw or preprocessed sensor output signals to the processing circuit 12, which processes the received sensor output signals to detect the occurrence of a fall. The fall detection circuit 13 may be incorporated into the housing 19 with the orientation sensor 14 to form a self-contained unit as illustrated in FIG. 2. Alternatively, the fall detection circuit 13 may be contained in a remote unit 30 that is also carried by the user as illustrated in FIG. 1. In this case, the main unit 10 containing the processing circuit 12 and the remote unit 30 containing the fall detection circuit 13 may be connected by a wired or wireless link.

The orientation sensor 14 measures the instantaneous orientation of the device 10. The orientation is an angle of slope, elevation, or depression of the device 10 with respect to gravity in one or more axes. In one embodiment, the orientation sensor 14 comprises an accelerometer that measures the proper acceleration of the device 10. The device 10 may include a single accelerometer that measures the orientation along one or more axes. The device 10 may also include two or more accelerometers that each measures the orientation along different axes. In one embodiment, the orientation sensor 14 comprises a low-g accelerometer (e.g. +/−2 g) that measures the orientation along three separate axes. The low-G setting enables the accelerometer to detect inclination values with sufficient sensitivity and resolution when the device 10 is relatively static. A specific example is the Model No. KXTF9-1026+/−2 g Tri-Axis Digital Accelerometer available from Kionix, Inc.

The alarm transmission circuit 15 sends an alarm signal to a third party in the event of a fall. The alarm transmission circuit 15 may comprise any wireless transmitter circuit, such as a social alarm transmitter, BLUETOOTH transmitter, WiFi transmitter, cordless phone transceiver, or Zigbee transmitter. In some embodiments, a bi-directional wireless transceiver may be used for two-way communication with the base unit.

The power supply 11 provides power to the device 10. The power supply 11 may comprise a rechargeable battery, such as a lithium battery or nickel-cadmium battery. Non-rechargeable batteries may also be used.

The indicator 17 indicates to the user that an alarm signal has been sent to the base unit. The indicator 17 may include an LCD display that displays a message, a light, or a vibration mechanism that are each capable of notifying the user regarding the sent alarm signal.

The input 18 enables the user to send a cancellation signal to the base unit to indicate a false alarm, or that help is not needed. The input 18 may comprise a switch or other like mechanism that the user can depress upon the occurrence of an inadvertent alarm signal being sent to the third party. In one exemplary embodiment, the processing circuit 12 can be programmed to send a signal responsive to a predetermined movement of the device 10. For example, the processing circuit 12 may send a cancellation signal when the user lifts the device 10 over the user's head, holds it for three seconds, then lowers the device 10.

One use scenario for the indicator 17 and input 18 is when the user suddenly sits down in a chair which may cause a false positive alarm (i.e., the user did not actually fall). The user in this example is able to determine that an alarm signal was sent to the third party and can cancel the signal by activating the input 18 within a predetermined period of time. The system may also be configured to require the user to contact the third party and verify that there was no fall occurrence.

As previously indicated, the device 10 can be incorporated into a watch or other useful device. Where the device 10 also functions as a watch, the housing 19 may also contain a watch dial or other time display 23, a timing-keeping circuit or device 22, and power supply 21. The display 23 may include traditional watch hands, or may include an LCD display or other digital display. The associated timing device 22 may comprise either a mechanical time keeping mechanism or a digital timing circuit. The power supply 21 may be the same as or different than the power supply 11 described above. The time keeping features add to the utility and aesthetics of the device 10 and discreetly hide the fall detection functionality of the device 10.

In use, the processing circuit 12 uses the output of the orientation sensor 14 to confirm a fall after an initial fall indication is received from the fall detection circuit 13 or is made based on the sensor output signals from the fall detection circuit 13. As previously noted, the orientation sensor 14 measures the orientation of the device 10 with respect to gravity relative to one or more axes before, during, and after a fall. Some embodiments measure a single angle of inclination relative a single axis. Preferably, the device 10 measures angles of inclination relative to two or more different axes. A preferred embodiment measures angles of inclination relative to three orthogonal axes. The orientations before the fall are compared to the orientations during and/or after the fall to confirm the initial fall indication.

Figure 3A:
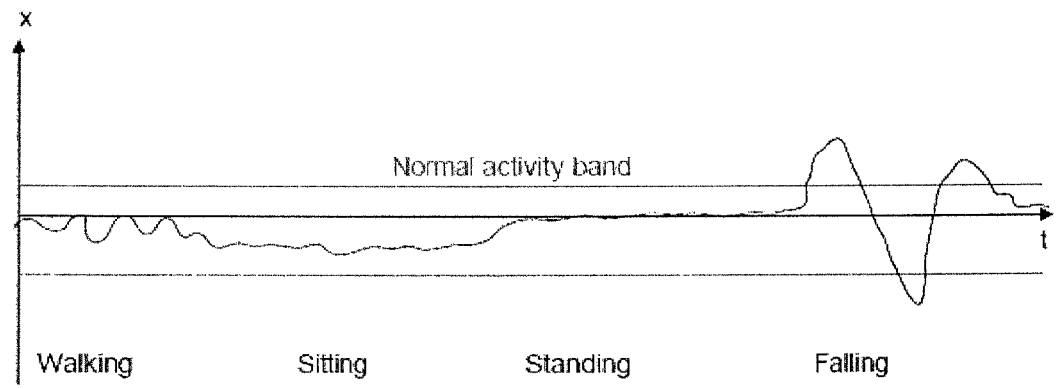
FIG. 3A is a graph over a period of time showing an inclination of a fall detection device relative to an x-axis.
Figure 3B:
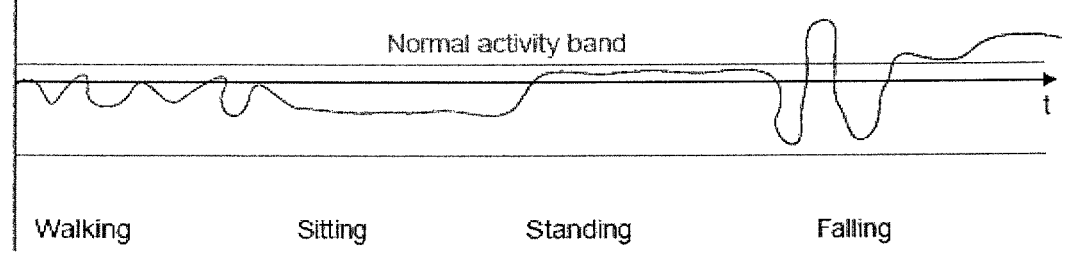
FIG. 3B is a graph over a period of time showing an inclination of a fall detection device relative to a y-axis.
Figure 3C:
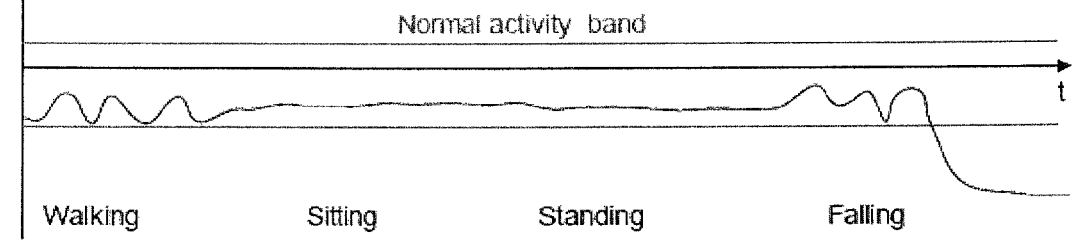
FIG. 3C is a graph over a period of time showing an inclination of a fall detection device relative to a z-axis.

FIGS. 3A, 3B, and 3C illustrate the instantaneous angles of orientation of the user relative to the respective axes for a person engaged in various activities. FIG. 3A includes a first angle of inclination relative to axis x. FIG. 3B includes a second angle of inclination relative to axis y. FIG. 3C includes a third angle of inclination relative to axis z. During various normal activities, the angles of inclination remain within a relatively narrow range along each of the three axes. The Figures illustrate the activities as including walking, sitting, and standing, although various other activities may be included and result in a relatively narrow range of inclinations. The occurrence of a fall causes one or more of the angles of inclination to go outside of the narrow range. These excessive angles of inclination that occur during the fall and/or after the fall are used by the device 10 to verify a fall occurrence.

Figure 4:
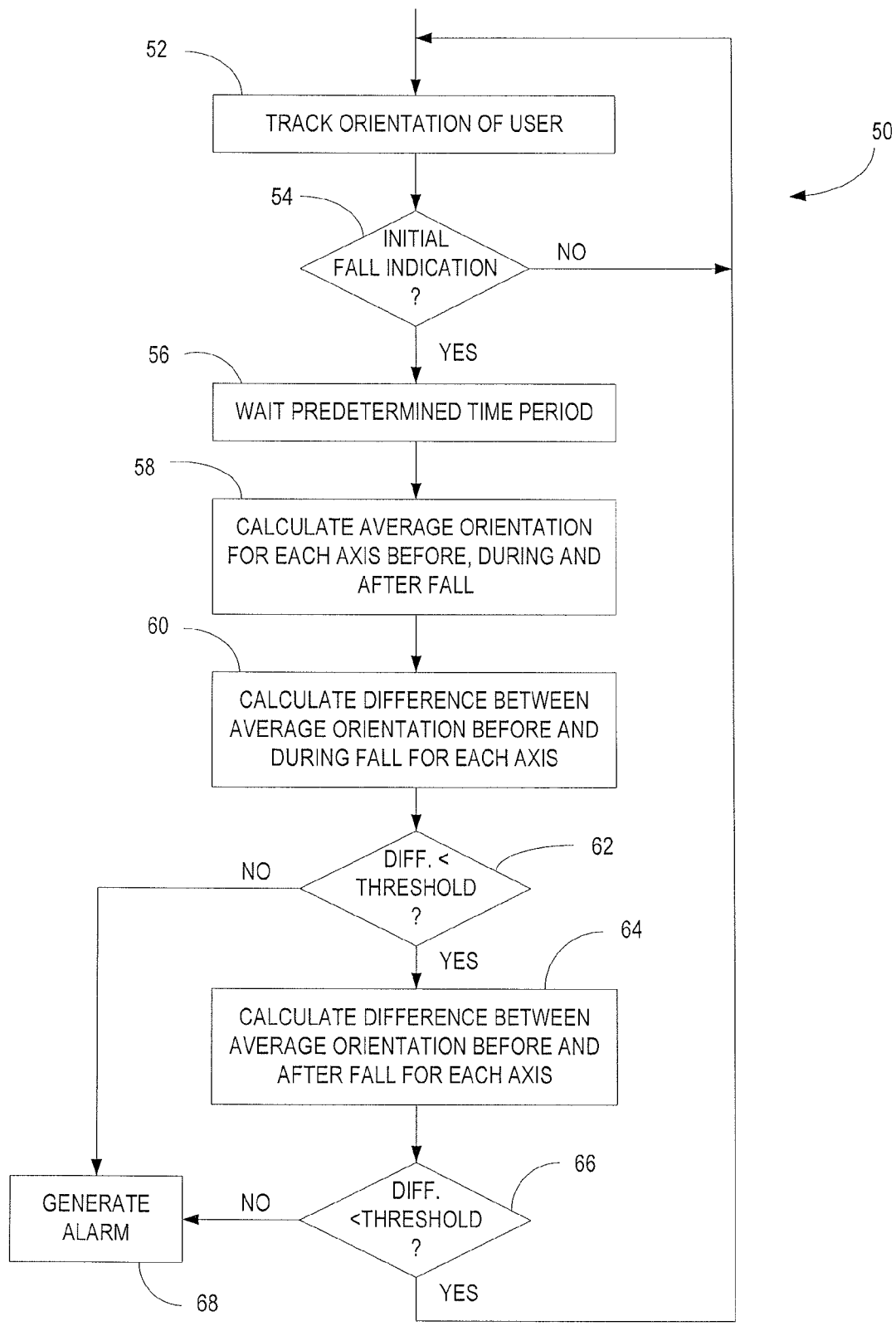
FIG. 4 illustrates an exemplary method of determining an occurrence of a fall.

One method 50 of confirming a fall event by a user is illustrated in FIG. 4. Initially, the device 10 is worn by the user and tracks the angles of inclination over the one or more axes (step 52). For purposes of explanation of this method, the device 10 tracks the orientation relative to three axes: x, y, and z, as previously described. The device 10 determines the orientation relative to the axes as the device 10 is worn by the user. The data samples are stored in a memory that is associated with the processing circuit 12. In one exemplary embodiment, the memory stores data samples for a predetermined period of time with the older data samples being deleted or overwritten. In other embodiments, the memory may be configured to store data samples for the entire time the user wears the device 10.

The device 10 may use various sampling rates depending upon the application. In one specific embodiment, the device 10 has a sampling rate of 3 Hz. In this example, the device takes three data samples per second for each axis for a total of nine samples per second. Faster or slower sampling rates may also be used. In one embodiment, the sampling rate remains constant while the device 10 is activated. Other embodiments may vary the sampling rate. For example, the device may increase the sampling rate upon receipt of an initial fall detection.

While the device 10 is worn by the user, the device 10 receives an initial indication of a fall event from the fall detection circuit 13 (step 54). As stated above, the fall detection circuit 13 may be incorporated into the device 10, or may be a separate unit that is also worn by the user. After receiving the fall event indication, the device 10 continues to sample the orientation for a predetermined period of time (e.g., ten seconds after the initial fall indication) (step 56). This time period may be shorter (e.g., 2 seconds) or longer (e.g., 20 seconds) depending on the application.

The angles of inclination for each of the three axes for a predetermined period (e.g., 20 seconds) of time are saved by the device 10. In one embodiment, the values for the last twenty seconds are saved at a sampling rate of 3 Hz, resulting in a total of sixty data samples for each of the three axes. Various other time durations and sampling rates may be used depending upon the application. The saved data samples include angles of inclination before, during, and after the fall. The period during the fall may be assumed to be a fixed time period (e.g. 2 sec.) immediately preceding the fall indication, or a fixed time period that brackets the fall indication (e.g. +/−1 sec). The periods before and after the fall may be contiguous or non-contiguous time periods.

Figure 5:
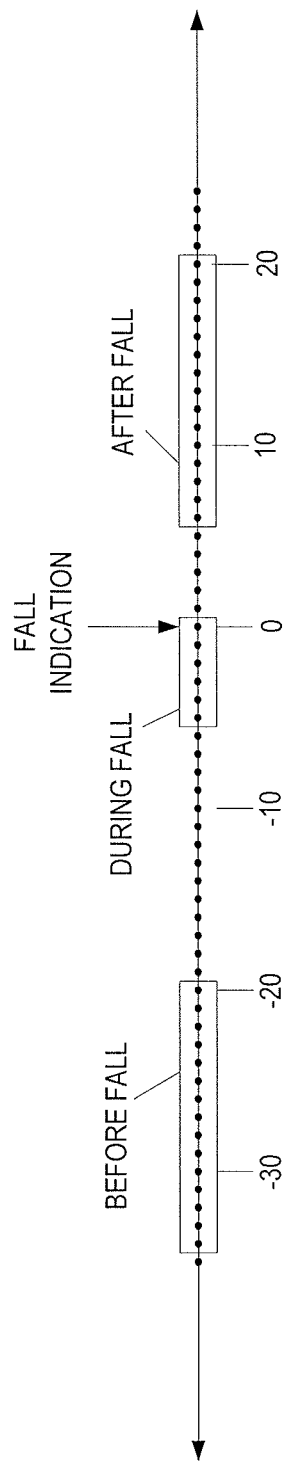
FIG. 5 is a timeline showing data samples collected before, during and after a fall.

To confirm the initial fall indication, the device 10 compares the orientations of the device before the fall to the orientations during and/or after the fall. More particularly, the processing circuit 12 computes the average orientation of the device 10 for each axis before the fall, during the fall and after the fall (block 58). The averaging of the measurements performs a form of filtering to filter out the dynamic component of the inclination measurements and obtain the static component of the user's orientation despite movements of the user. As one example, the processing circuit 12 may select data samples for a five second period before the fall, a two second period during the fall, and a five second period after the fall as shown in FIG. 5. This embodiment will have a total of fifteen values for the average before the fall for each axis (five second time frame at three samples per second), six values for the average during the fall for each axis (two second time frame at three samples per second), and fifteen values for the average after the fall for each axis (five second time frame at three samples per second). Therefore, the averages are determined as follows:

$$X_{before} = \Sigma(x_{-34} + x_{-33} + x_{-32} \ldots + x_{-20})/15 \quad \text{(Eq. 1)}$$

$$Y_{before} = \Sigma(y_{-34} + y_{-33} + y_{-32} \ldots + y_{-20})/15 \quad \text{(Eq. 2)}$$

$$Z_{before} = \Sigma(z_{-34} + z_{-33} + z_{-32} \ldots + z_{-20})/15 \quad \text{(Eq. 3)}$$

$$X_{during} = \Sigma(x_{-5} + x_{-4} + x_{-3} \ldots + x_0)/6 \quad \text{(Eq. 4)}$$

$$Y_{during}=\Sigma(y_{-5}+y_{-4}+y_{-3}\ldots+y_0)/6 \quad (Eq.\ 5)$$

$$Z_{during}=\Sigma(z_{-5}+z_{-4}+z_{-3}\ldots+z_0)/6 \quad (Eq.\ 6)$$

$$X_{after}=\Sigma(x_6+x_7+x_8\ldots+x_{20})/15 \quad (Eq.\ 7)$$

$$Y_{after}=\Sigma(y_6+y_7+y_8\ldots+y_{20})/15 \quad (Eq.\ 8)$$

$$Z_{after}=\Sigma(z_6+z_7+z_8\ldots+z_{20})/15 \quad (Eq.\ 9)$$

The average orientation of the device 10 before the fall is used as a baseline for comparison with the average orientation during the fall and/or after the fall. Returning to the flowchart of FIG. 4, the processing circuit 12 calculates, for each axis, an absolute value of the difference between the average before and during the fall (block 60). These values are determined by the following equations:

$$DiffA=|X_{during}-X_{before}| \quad (Eq.\ 10)$$

$$DiffB=|Y_{during}-Y_{before}| \quad (Eq.\ 11)$$

$$DiffC=|Z_{during}-Z_{before}| \quad (Eq.\ 12)$$

These differences are then compared to a threshold for each axis (block 62). In some embodiments, the same threshold may be applied to all three axes. In other embodiments, different thresholds may be used for different axes. The thresholds may be determined form empirical data. Based on the comparison, the processing circuit 12 may confirm that a fall has occurred. If any of the differences are greater than the respective threshold, then a fall occurrence is detected and an alarm signal is sent to a third party (block 68). If the differences are not greater than the respective thresholds, additional processing may optionally be applied. In the exemplary embodiment shown in FIG. 4, a second difference is calculated between the average orientations before and after the initial fall (block 64). These values are determined by the following equations:

$$DiffD=|X_{after}-X_{before}| \quad (Eq.\ 13)$$

$$DiffE=|Y_{after}-Y_{before}| \quad (Eq.\ 14)$$

$$DiffF=|Z_{after}-Z_{before}| \quad (Eq.\ 15)$$

These differences are compared to a second set of thresholds for each axis (block 66). If any of the differences are greater than the respective threshold levels, then a fall occurrence is detected and an alarm signal is sent to the third party (block 68). If the differences are below the respective threshold levels, it is determined that a fall has not occurred and the system returns to await another initial fall detection.

The threshold values used for comparison in may be factory preset values that are pre-stored in memory in the processing circuit 12. Alternatively, the threshold values may be based upon previous data collected while the device 10 is being worn by the user and then stored in memory in the processing circuit 12.

The exemplary embodiment shown in FIG. 4 determines that a fall has occurred if any of the axes are above the respective thresholds. Other embodiments may determine that a fall has occurred when the data is outside two or more of the axes.

The exemplary embodiment herein determines orientation along three axes of inclination. Other embodiments may determine orientation over fewer than three or more than three axes of inclination.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of using a device to detect a fall by a user, said method comprising:

continuously receiving, from an orientation sensor that includes an accelerometer, inclination signals indicative of measurements of an inclination of the device relative to one or more different axes while the device is being worn by the user;

saving said measurements for a predetermined time period;

receiving, from a pressure sensor, pressure signals indicative of measurements of an atmospheric pressure at the device;

determining an initial indication of a fall based on changes in the received pressure signals;

responsive to determining the initial indication of the fall, determining, using said measurements from the orientation sensor in the device that includes the accelerometer, an inclination of the device worn by the user relative to one or more different axes at each of a first plurality of time instants in a first time period before the initial indication of the fall and an inclination of the device at each of a second plurality of time instants in a second time period, the second plurality of time instants occurring during a fixed time period of the second time period immediately preceding the initial indication of the fall and after the first plurality of time instants, the orientation sensor being distinct from the pressure sensor and with determining the inclinations of the device being performed in real time and while receiving the inclination signals from the orientation sensor;

responsive to determining the initial indication of the fall, comparing the inclination of the device in the second time period to the inclination of the device in the first time period; and verifying that the fail has occurred based on said comparison.

2. The method of claim 1, wherein comparing the inclination of the device in the second time period to the inclination of the device in the first time period comprises:

calculating an average inclination of the device from the first plurality of time instants;

calculating an average inclination of the device from the second plurality of time instants; and calculating a difference between the average inclination of the device from the second plurality of time instants and the average inclination of the device from the first plurality of time instants.

3. The method of claim 2, wherein verifying that the fall has occurred based on said comparison comprises:
determining that the fall has occurred if the difference exceeds a threshold; and
determining that the fall has not occurred if the difference is less than the threshold.

4. The method of claim 1 further comprising:
measuring an inclination of the device relative to one or more different axes for a third plurality of time instants in a third time period that is after the second time period;
responsive to the initial indication, comparing the inclination of the device in the third time period to the inclination of the device in the first time period; and
verifying that the fall has occurred based on said comparing the inclination of the device in the third time period to the inclination of the device in the first time period.

5. The method of claim 4, wherein comparing the inclination of the device in the third time period to the inclination of the device in the first time period comprises:
calculating an average inclination of the device from the third plurality of time instants; and
calculating a difference between the average inclination of the device in the third time period and the average inclination of the device in the first time period.

6. The method of claim 5, wherein verifying that the fall occurred based on said comparing the inclination of the device in the third time period to the inclination of the device in the first time period comprises:
determining that the fall has occurred if the difference exceeds a threshold; and
determining that the fall has not occurred if the difference is less than the threshold.

7. The method of claim 1, wherein measuring the inclinations of the device relative to one or more different axes comprises measuring the inclinations of the device relative to three orthogonal axes.

8. The method of claim 7, wherein measuring the inclinations of the device comprises measuring the inclinations of the device relative to the three orthogonal axes using the accelerometer which is a single three-axis accelerometer.

9. A method of using a device to detect a fall by a user, said method comprising:
continuously receiving, from an orientation sensor that includes an accelerometer, inclination signals indicative of measurements of an inclination of the device relative to one or more different axes while the device is being worn by the user; saving said measurements for a predetermined time period;
receiving, from a pressure sensor, pressure signals indicative of measurements of an atmospheric pressure at the device;
determining an initial indication of a fall with a fall detection circuit in the device that includes the pressure sensor with the initial indication of the fall based on changes in the pressure signals;
responsive to determining the initial indication of the fall, determining in real time and while receiving the inclination signals from the orientation sensor and using said measurements from the orientation sensor in the device that includes the accelerometer, an inclination of the device at each of a first plurality of time instants in a first time period before the initial indication of the fall, an inclination of the device at each of a second plurality of time instants in a second time period during the fall that is a fixed time period immediately preceding the initial indication and after the first plurality of time instants, and an inclination of the device at each of a third plurality of time instants in a third time period after the initial indication of the fall;
calculating an average inclination for each of the one or more axes for the first time period, the second time period, and the third time period;
calculating a first difference between the average inclination for the second time period and the average inclination for the first time period for at least one of the axes;
calculating a second difference between the average inclination for the third time period and the average inclination for the first time period for at least one of the axes; and
verifying that the fall has occurred if the first or second difference exceeds a threshold.

10. The method of claim 9, wherein receiving the initial indication of the fall includes receiving a signal from the device worn by the user.

11. The method of claim 9, wherein measuring the inclinations of the device relative to one or more different axes comprises measuring the inclinations of the device relative to three orthogonal axes.

12. The method of claim 11, wherein the accelerometer used for measuring the inclinations of the device comprises a single three-axis accelerometer.

13. A fall detection device that is worn by a user comprising:
a fall detection circuit with a pressure sensor to provide an initial indication of a fall based on changes in measured atmospheric pressure;
an orientation sensor with an accelerometer to measure an inclination of the user; the orientation sensor being distinct from the fall detection circuit;
a verification circuit for verifying that a fall has occurred; said verification circuit configured to:
receive the initial indication of the fall from the fall detection circuit;
in real time and while receiving the measurements of the orientation sensor, determine, responsive to receiving the initial indication of the fall from the fall detection circuit, an inclination of the device relative to one or more different axes for each of a first plurality of time instants and an inclination of the device at each of a second plurality of time instants that is after the first plurality of time instants, the second plurality of time instants being a fixed time period immediately preceding the initial indication of the fall;
compare, responsive to receiving the initial indication of the fall from the fall detection circuit, the inclination of the device during the second plurality of time instants to the inclination of the device during the first plurality of time instants; and
verify that the fall has occurred based on said comparison.

14. The fall detection device of claim 13, wherein the verification circuit compares the inclination of the device during the second plurality of time instants to the inclination of the device during the first plurality of time instants by:
calculating an average inclination of the device from the first plurality of measurements;

calculating an average inclination of the device from the second plurality of measurements; and calculating a difference between the average inclination of the device during the second plurality of time instants and the average inclination of the device during the first plurality of time instants.

15. The fall detection device of claim 14, wherein the verification circuit verifies that the fall occurred based on a comparison of the inclination of the device during the second plurality of time instants to the inclination of the device during the first plurality of time instants by:

determining that the fall has occurred if the difference exceeds a threshold; and determining that the fall has not occurred if the difference is less than the threshold.

16. The fall detection device of claim 13, wherein the verification circuit is further configured to:

measure an inclination of the device relative to one or more different axes for a third plurality of time instants after the second plurality of time instants;

compare, responsive to the initial indication, the inclination of the device during the third plurality of time instants to the inclination of the device during the first plurality of time instants; and verify that the fall occurred based on said comparing the inclination of the device during the third plurality of time instants to the inclination of the device during the first plurality of time instants.

17. The fall detection device of claim 16, wherein the verification circuit compares the inclination of the device during the third plurality of time instants to the inclination of the device during the first plurality of time instants by:

calculating an average inclination of the device from the third plurality of time instants; and calculating a difference between the average inclination of the device during the third plurality of time instants and the average inclination of the device during the first plurality of time instants.

18. The fall detection device of claim 17, wherein the verification circuit verifies that a fall occurred based on a comparison of the inclination of the device during the third plurality of time instants to the inclination of the device during the first plurality of time instants by:

determining that the fail has occurred if the difference exceeds a threshold; and determining that the fall has not occurred if the difference is less than the threshold.

19. The fall detection device of claim 13 wherein the fall detection circuit and orientation sensor are contained in a common housing.

* * * * *